United States Patent
Li et al.

(10) Patent No.: US 11,935,639 B2
(45) Date of Patent: Mar. 19, 2024

(54) AUGMENTED REALITY INTERACTIVE REHABILITATION SYSTEM

(71) Applicants: Ping-Chia Li, Kaohsiung (TW); Jyh-Bin Suen, Kaohsiung (TW); Wan-Chien Yang, Kaohsiung (TW)

(72) Inventors: Ping-Chia Li, Kaohsiung (TW); Jyh-Bin Suen, Kaohsiung (TW); Wan-Chien Yang, Kaohsiung (TW)

( * ) Notice: Subject to any disclaimer, the term of this patent is extended or adjusted under 35 U.S.C. 154(b) by 431 days.

(21) Appl. No.: 17/403,163

(22) Filed: Aug. 16, 2021

(65) Prior Publication Data
US 2022/0139521 A1    May 5, 2022

(30) Foreign Application Priority Data

Oct. 29, 2020  (TW) .................... 109137682

(51) Int. Cl.
| | |
|---|---|
| *G16H 20/30* | (2018.01) |
| *G02B 27/01* | (2006.01) |
| *G06F 3/01* | (2006.01) |
| *G06T 19/00* | (2011.01) |

(52) U.S. Cl.
CPC .......... *G16H 20/30* (2018.01); *G02B 27/017* (2013.01); *G06F 3/011* (2013.01); *G06F 3/016* (2013.01); *G06F 3/017* (2013.01); *G06T 19/006* (2013.01); *G02B 2027/0178* (2013.01)

(58) Field of Classification Search
CPC .................. G16H 20/30; G02B 27/017; G02B 2027/014; G02B 2027/0178; G06F 3/011; G06F 3/016; G06F 3/017; G06T 19/006; A61H 1/00; A63B 24/00; G09B 9/00; G09B 19/003
See application file for complete search history.

(56) References Cited

U.S. PATENT DOCUMENTS

2019/0279519 A1    9/2019  Somareddy

FOREIGN PATENT DOCUMENTS

| CN | 111773539 | A |   | 10/2020 | |
|---|---|---|---|---|---|
| EP | 3251152 | B1 | * | 8/2021 | ........... A63F 13/213 |
| KR | 102046745 | B1 | * | 11/2019 | |
| KR | 20220033213 | A | * | 3/2022 | |
| TW | M582674 | U |   | 8/2019 | |
| TW | M606989 | U | * | 1/2021 | |
| TW | I726827 | B | * | 5/2021 | |
| WO | WO-2015162528 | A1 | * | 10/2015 | ............... G01C 3/08 |
| WO | 2018064213 | A1 |   | 4/2018 | |

OTHER PUBLICATIONS

Search Report appended to an Office Action, which was issued to Taiwanese counterpart application No. 109137682 by the TIPO dated Feb. 24, 2021, with an English translation thereof.

* cited by examiner

*Primary Examiner* — Chante E Harrison
(74) *Attorney, Agent, or Firm* — Muncy, Geissler, Olds & Lowe, P.C.

(57) ABSTRACT

An augmented reality interactive rehabilitation system includes an augmented reality eyewear device, a holding seat, a haptic module and sensing modules. The holding seat has a first recess and a second recess smaller in cross section than the first recess. The haptic module is removably placeable into the holding seat, and has a first end to be received in the first recess and a second end to be received in the second recess. The sensing modules are informationally connected to the augmented reality eyewear device and disposed in the holding seat to detect whether the haptic module is placed in a correct position.

12 Claims, 6 Drawing Sheets

AUGMENTED REALITY INTERACTIVE REHABILITATION SYSTEM

CROSS-REFERENCE TO RELATED APPLICATION

This application claims priority to Taiwanese Patent Application No. 109137682, filed on Oct. 29, 2020.

FIELD

The disclosure relates to a rehabilitation system, and more particularly to an augmented reality interactive rehabilitation system.

BACKGROUND

A rehabilitation therapist generally works with patients one by one to help them perform rehabilitation activities and exercises.

However, the number of therapists in a rehabilitation center is usually insufficient to provide their services for a large number of patients. Although a person to person service can provide a better rehabilitation result, it can impose large physical and mental burdens on a rehabilitation therapist. In addition, a patient, in some cases, must experience a long waiting time to queue for meeting a therapist who is assigned to assist him/her in performing rehabilitation exercises and/or receiving rehabilitation treatments.

SUMMARY

Therefore, an object of the present disclosure is to provide an augmented reality interactive rehabilitation system that aids in rehabilitation.

According to this disclosure, an augmented reality interactive rehabilitation system includes a wearing unit and a haptic tool unit.

The wearing unit is configured to be worn by a user, and includes an augmented reality eyewear device capable of providing an augmented reality image and an identification module connected to the augmented reality eyewear device and configured to identify user activities.

The haptic tool unit includes a holding seat, at least one haptic module, and a plurality of sensing modules.

The holding seat has a top surface, a first recess wall, a second recess wall, and an annular shoulder face. The first recess wall extends downwardly from the top surface and surrounds a first recess. The second recess wall extends downwardly below the first recess wall and surrounds a second recess smaller in cross section than the first recess. The annular shoulder face is formed between the first and second recesses, and has an outer periphery connected to a bottom end of the first recess wall, and an inner periphery connected to a top end of the second recess wall. A recess bottom surface is below the second recess.

The at least one haptic module is removably placeable into the holding seat and configured to be held by the user. The at least one haptic module has a first end to be received in the first recess, and a second end to be received in the second recess.

The sensing modules is informationally connected to the wearing unit and disposed in the holding seat to detect whether the at least one haptic module is properly placed.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
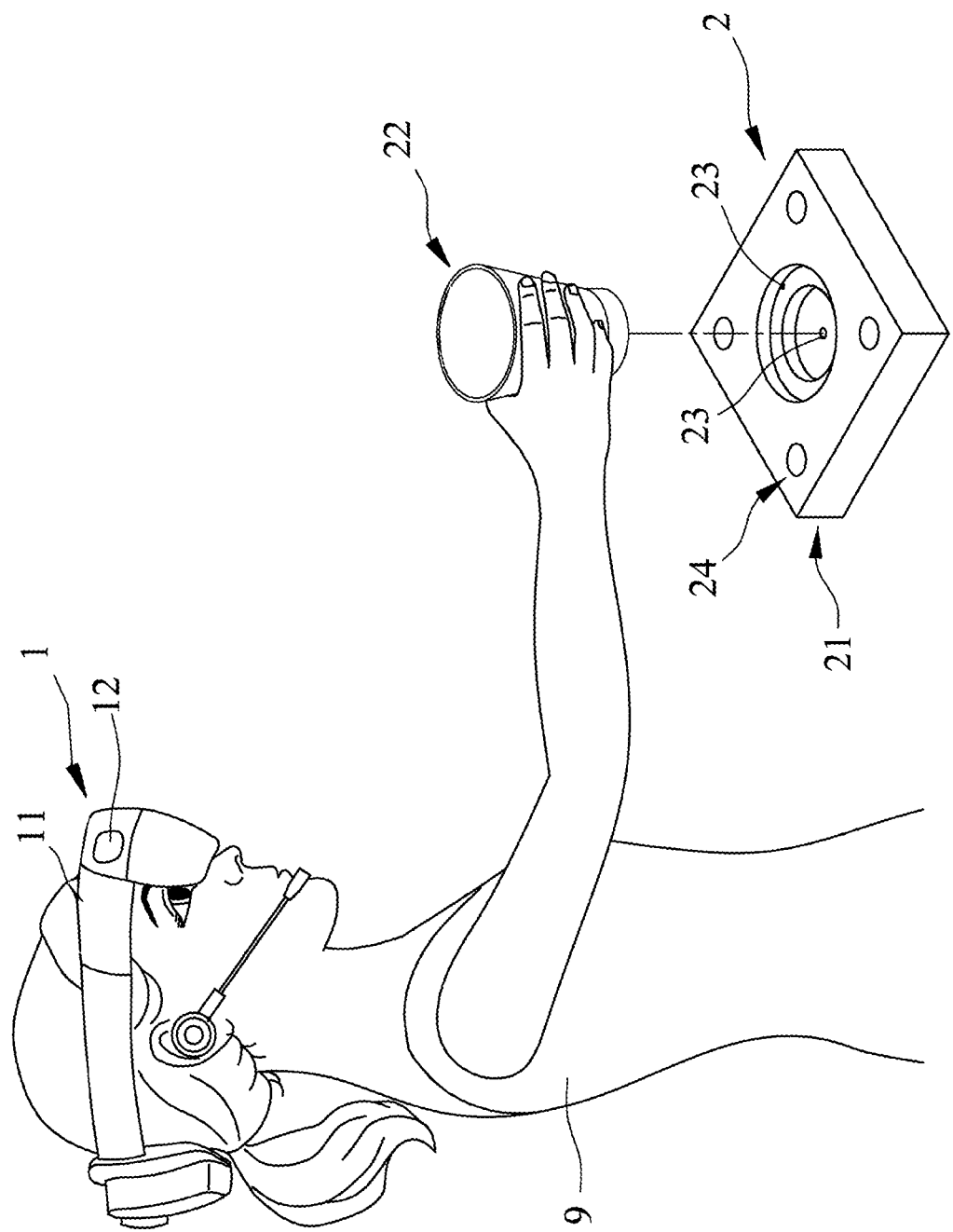
FIG. 1 illustrates an augmented reality interactive rehabilitation system according to an embodiment of the present disclosure in use by a user.

FIG. 1 illustrates an augmented reality interactive rehabilitation system according to an embodiment of the disclosure. The augmented reality interactive rehabilitation system includes a wearing unit 1 configured to be worn by a user 9, and a haptic tool unit 2.

The wearing unit 1 includes an augmented reality eyewear device 11 capable of providing an augmented reality image, and an identification module 12 connected to the augmented reality eyewear device 11 and configured to identify user hand activities from the user 9. In this embodiment, the augmented reality eyewear device 11 is a smart multimedia device in cooperation with an application program to provide visual and auditory augmented reality multimedia.

The identification module 12 is an image recognition device directly connected to the augmented reality eyewear device 11. The identification module 12 can, but not limited hereto, continuously capture hand movements of the user 9 to obtain images, and then perform analysis based on the captured images to provide a recognition result information.

The haptic tool unit 2 includes a holding seat 21, a plurality of haptic modules 22 (only one shown in FIG. 1), a plurality of sensing modules 23, and a cue module 24.

Figure 2:
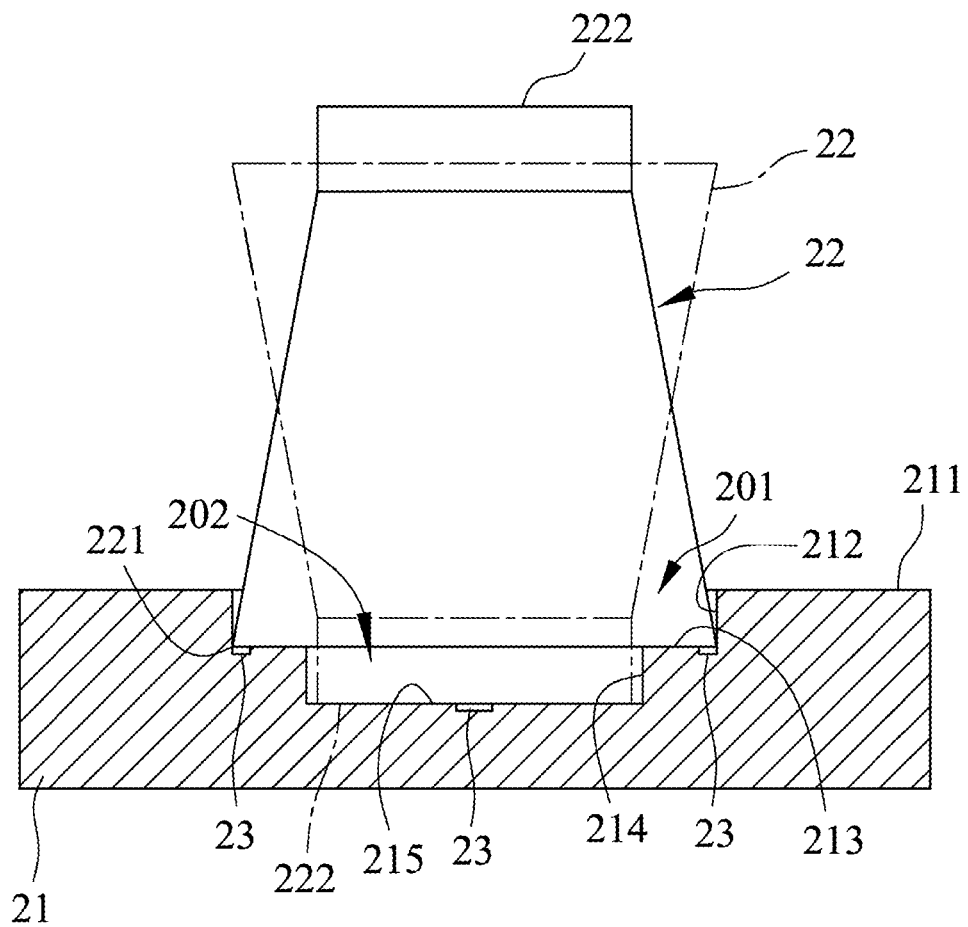
FIG. 2 is a side view of the embodiment illustrating a haptic module placeable into a holding seat.

As shown in FIGS. 1 and 2, the holding seat 21 has a top surface 211, a first recess wall 212, an annular shoulder face 213, a second recess wall 214, and a recess bottom surface 215. The first recess wall 212 extends downwardly from the top surface 211 and surrounds a first recess 201. The second recess wall 214 extends downwardly below the first recess wall 212 and surrounds a second recess 202 smaller in cross section than the first recess 201. The annular shoulder face 213 is formed between the first and second recesses 201, 202, and has an outer periphery connected to a bottom end of the first recess wall 212, and an inner periphery connected to a top end of the second recess wall 214. The recess bottom surface 215 is disposed below the second recess 202.

The sensing modules 23 are informationally connected to the wearing unit 1 and disposed in the holding seat 21 to detect whether the haptic module(s) 22 (further details of the haptic modules 22 will be described hereinafter) are properly placed. The cue module element 24 is disposed on the top surface 211 of the holding seat 21 for signalling that the haptic module 22 is properly placed into the holding seat.

In this embodiment the sensing modules 23 are disposed on the first recess wall 212 and the recess bottom surface

215. Each sensing module 23 is a pressure sensor or a proximity switch for detection of the situations occurring in the first and second recess 201, 202.

Figure 3:
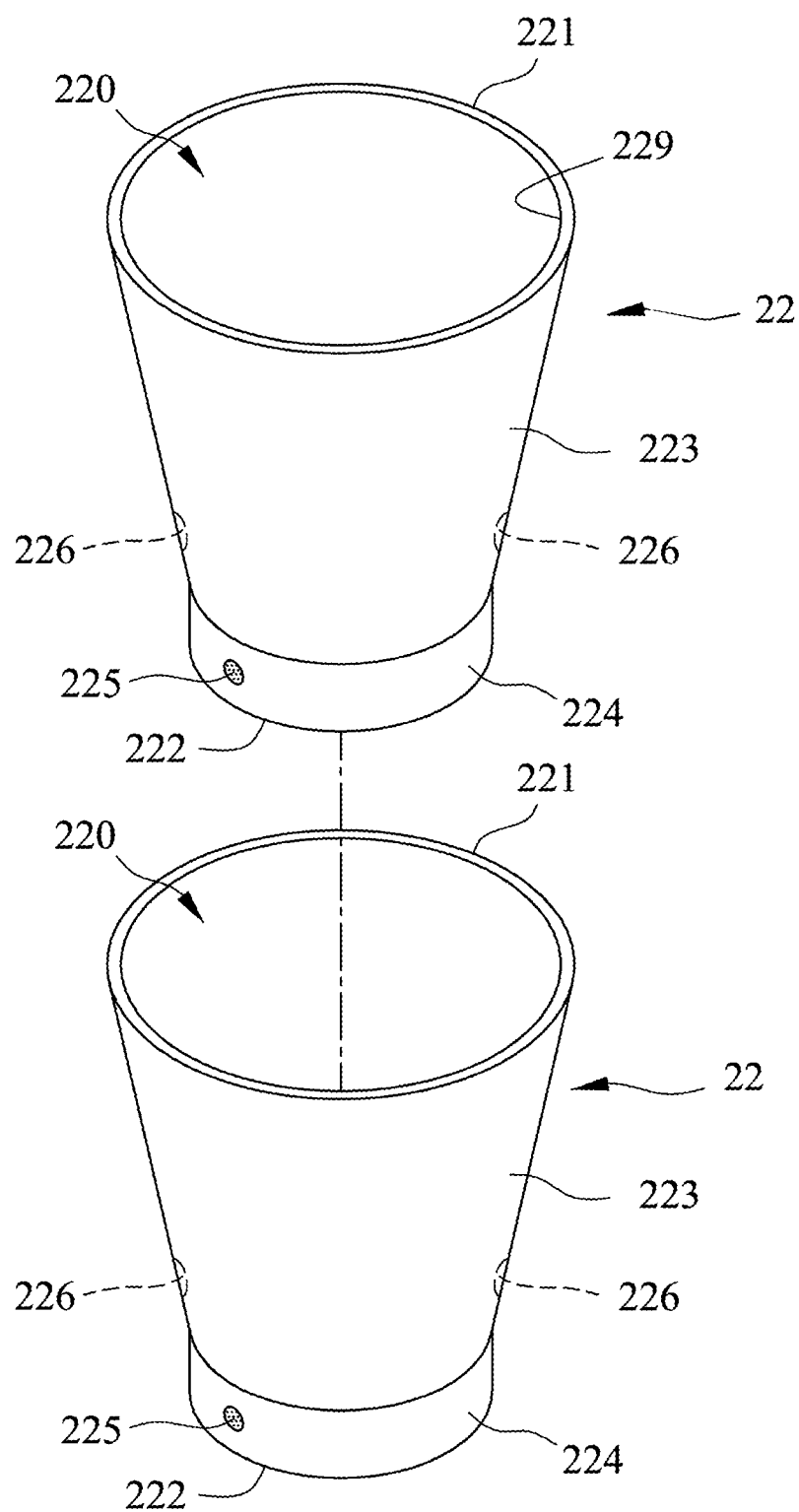
FIG. 3 is an exploded perspective view of the embodiment illustrating haptic modules to be stacked one on the other.

As shown in FIGS. 2 and 3, the haptic modules can be stacked one on the other. Each haptic module 22 can be held by the user 9 and is removably placeable into the holding seat 21. Each haptic module 22 has a main body 223, a cue light element 224, a speaker 225, and a plurality of receiving space sensors 226. The main body 223 has a first end 221 to be received in the first recess 201, a second end 222 to be received in the second recess 202, and a receiving space 220 that has an opening 229 surrounded by the first end 221. The cue light element 224 is disposed on the main body 223. The speaker 225 is disposed on the main body 223. The receiving space sensors 226 are disposed in the receiving space 220 to detect whether the receiving space 220 of one of the haptic modules receives the other one of the haptic modules 22 to form a stack, thereby ensuring that the haptic modules 22 are correctly stacked one on the other. In this embodiment, each haptic module 22 is in the form of a beverage cup. The opening 229 is the cup mouth surrounded by the first end 221. The second end 22 is the cup bottom end. The haptic modules 22 in cooperation with the holding seat 21 can be used by a patient to exercise cup-stacking activities which can rehabilitate mobility of the patient's hands. The cue light element 224 and the speaker 225 are able to cooperate with the holding seat 21 to produce the effect of scenario simulation and prompt guidance through emission of color light, flashing light, situational sounds, or prompt sounds.

Figure 4:
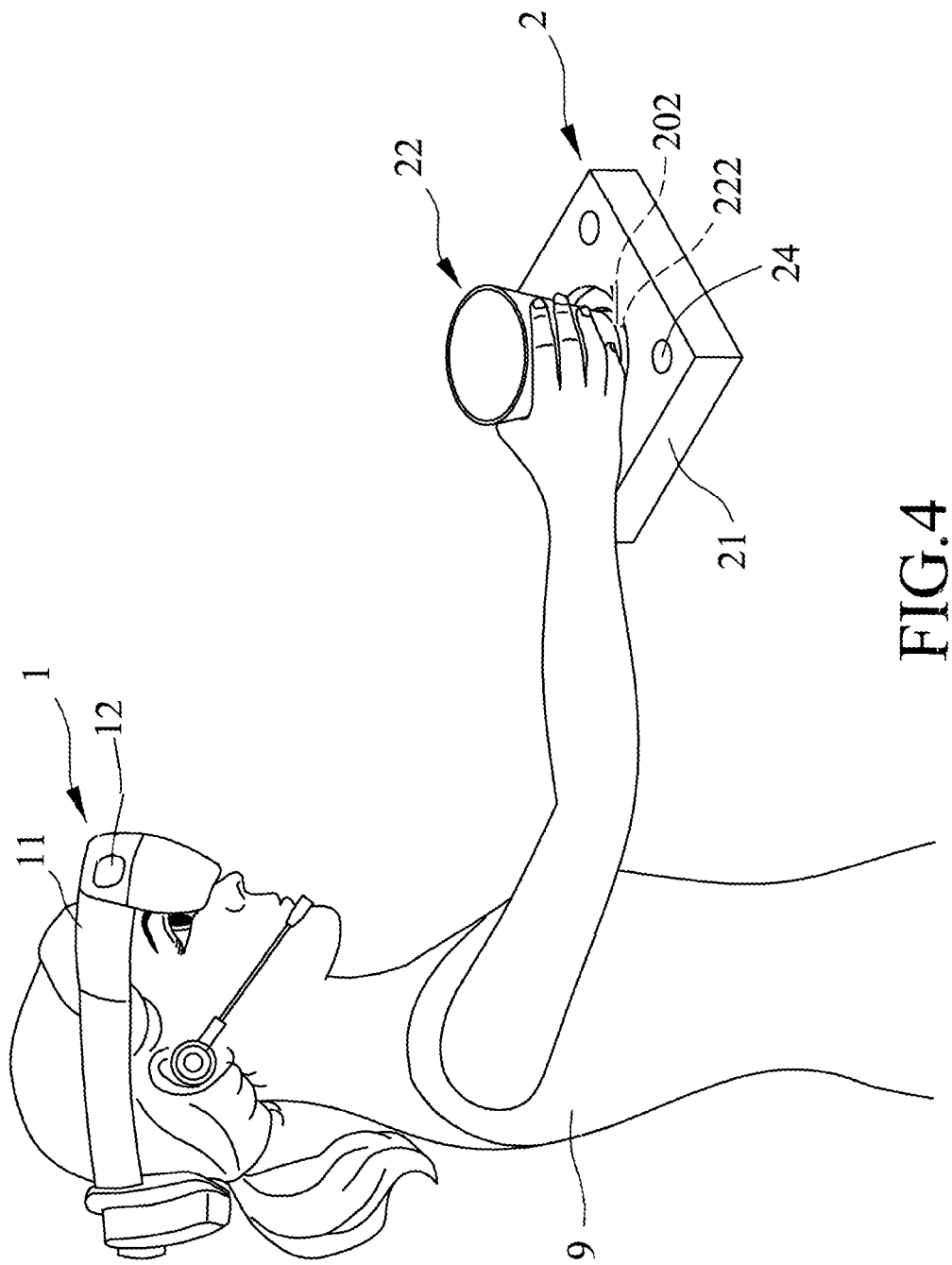
FIG. 4 of the embodiment illustrates the haptic module placed by the user into the holding seat.
Figure 5:
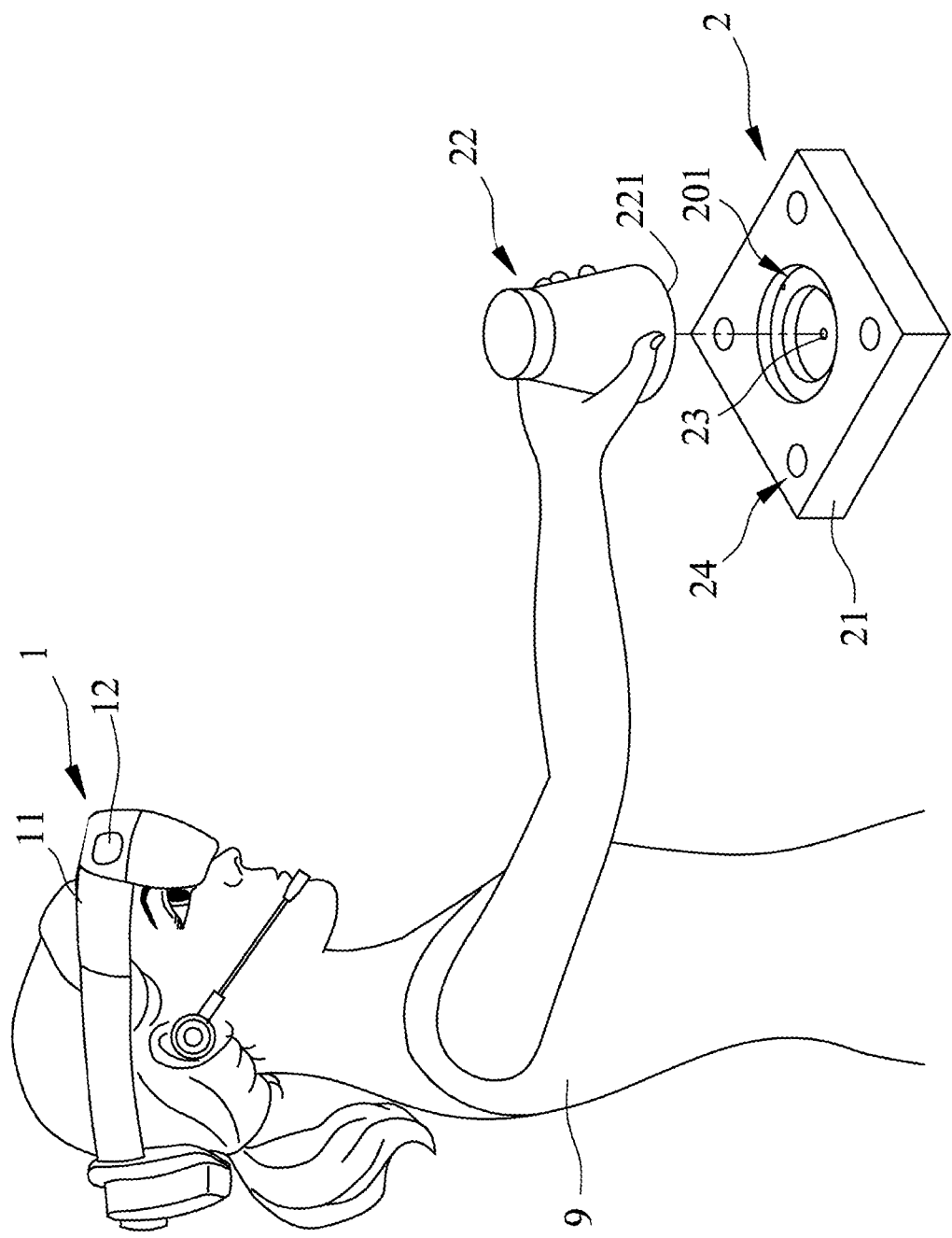
FIG. 5 of the embodiment illustrates the haptic module turned upside down by the user for placement into the holding seat.

Referring to FIGS. 4 and 5 in combination with FIG. 3, manipulation of the augmented reality interactive rehabilitation system of the disclosure is shown. In FIG. 4, the user 9 holds the haptic module 22, and tries to place the second end 222 thereof into the holding seat 21. When the second end 222 of the haptic module 22 is correctly placed in abutment with the second recess wall 214 and the recess bottom surface 215 of the holding seat. 21, the sensing modules 23 disposed on the recess bottom surface 215 can recognize that the haptic module 22 is placed correctly.

As shown in FIG. 5, the user 9 rotates his/her arm to place the first end 221 of the haptic module 22 into the first recess 201 of the holding seat 21. When the first end 221 is correctly placed into the first recess 201 and abuts the junction of the annular surface 213 and the first recess wall 212 (see FIG. 2), the sensing nodules 23 disposed on the first recess wall 212 are triggered and detect that the haptic module 22 is placed correctly.

In order that the user 9 can be more motivated to perform rehabilitation and have a sense of accomplishment in rehabilitation, the haptic modules 22 are configured to have the shape of a beverage cup, and the augmented reality eyewear device 11 is configured to produce images that display a simulation of a scene of a beverage shop. Particularly, when the identification module 12 identifies that a hand motion of the user 9 is to pick up one of the haptic modules 22, the augmented reality image provided by the augmented reality eyewear device 11 displays that beverage is prepared using a beverage cup. When the identification module 12 identifies that the hand motion of the user 9 is to place the haptic module in the holding seat 21, the augmented reality image shows that the beverage cup containing the beverage is handed to a customer, or the beverage cup after being washed is placed. In a ready use position. Upon completion of the hand motion of the user to place the haptic module(s) 22 into the holding seat 21, the cue module 24, which is configured to be a light source, will emit specific multicolored light based on the situations of the game process as displayed by the augmented reality image. The cue module 24, which is configured to be a fragrance release device to release a fragrance, a coffee aroma, for example, will stimulate the sense of smell of the user 9 so that the user will have a feel of being immersed in the game process.

Figure 6:
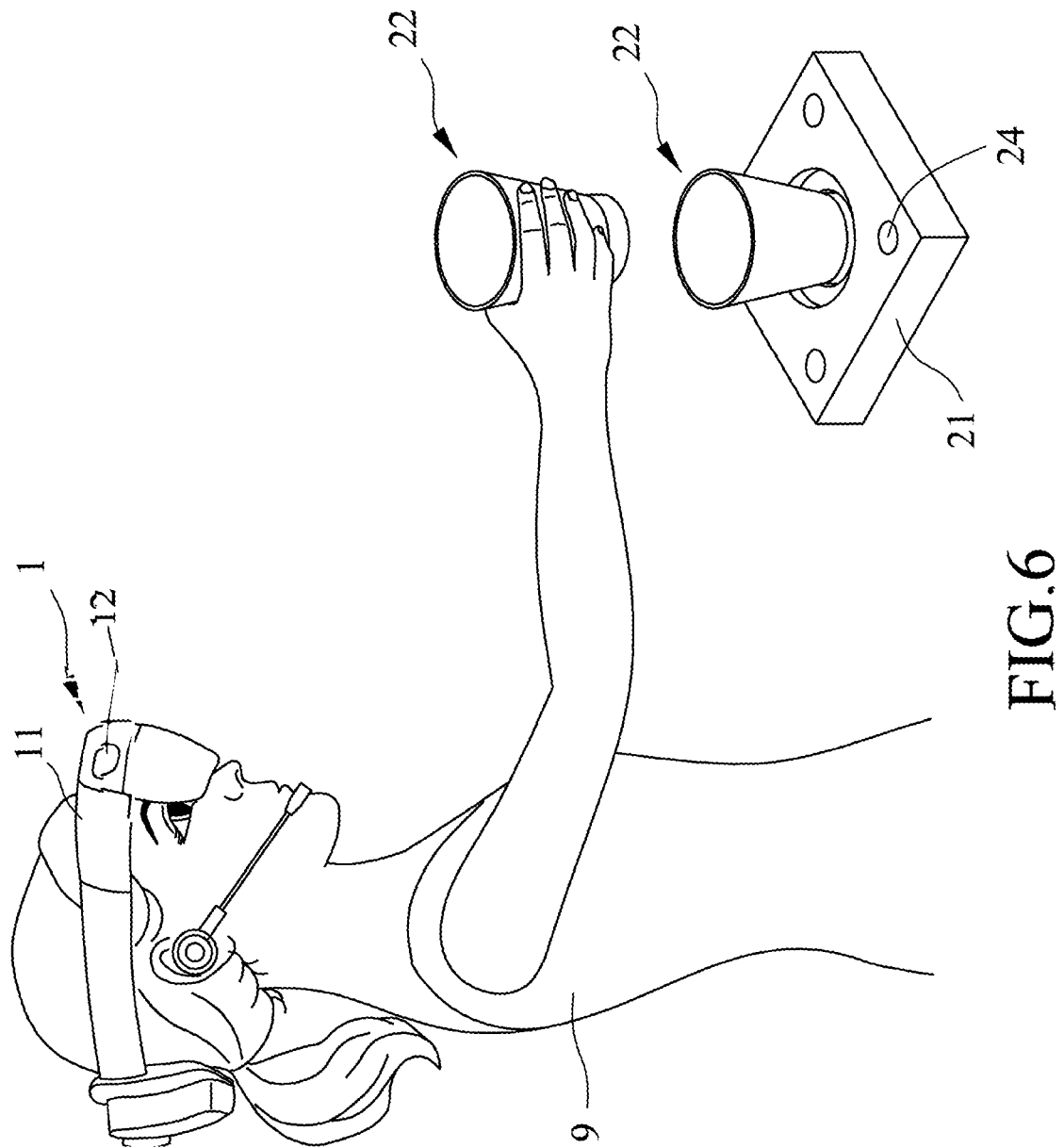
FIG. 6 of the embodiment illustrates haptic modules to be stacked one on the other in the holding seat by the user.

Referring to FIG. 6 in combination with FIGS. 2 and 3, an alternative method of manipulating the augmented reality interactive rehabilitation system of the disclosure is illustrated. As shown in FIGS. 3 and 6, the user performs rehabilitation by stacking the haptic modules 22 with the aid of the receiving space sensors 226 of the haptic modules 22. When the second end 222 of one of the haptic modules 22 is moved into the receiving space 220 of the other haptic module 22 to stack the haptic modules 22, the main body 223 of the haptic module 22 received in the receiving space 220 triggers the sensors 226 in the receiving space 220 of the other haptic module so that the sensors 226 detect that the haptic modules are correctly stacked one on the other. After the haptic modules 22 are stacked, the resulting stack is placed into the holding seat 21. During manipulation, the augmented reality eyewear device 11 provides the augmented reality simulation images, while the cue module 24 on the holding seat 21 functions to provide, depending on situational needs, colored light effects and/or fragrance emission.

Noteworthy, the haptic modules 22 each are not limited to having the beverage cup appearance, and the augmented reality eyewear device 11 not limited to providing the beverage shop environment simulation. The haptic modules 22 may have any other suitable configuration that enables the haptic modules 22 to be handheld and placed into the holding seat 21. Further, the augmented reality images provided by the augmented reality eyewear device 11 are adjustable.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An augmented reality interactive rehabilitation system, comprising,
   a wearing unit configured to be worn by a user and including
      an augmented reality eyewear device capable of providing an augmented reality image, and an identification module connected to said augmented reality eyewear device and configured to identify user hand activities; and a haptic tool unit including a holding seat having a top surface, a first recess wall extending downwardly from said top surface and surrounding a first recess, a second recess wall extending downwardly below said first recess wall and surrounding a second recess smaller in cross section than said first recess, and an annular shoulder face formed between said first and second recesses, and having an outer periphery connected to a bottom end of said first recess wall, and an inner periphery connected to a top end of said second recess wall, a recess bottom surface below said second recess, at least one haptic module removably placeable into said holding seat and configured to be held by the user, said at least one haptic module having a first end to be received in said first recess, and a second end to be received in said second recess, and a plurality of sensing modules informationally connected to said wearing unit and disposed in said holding seat to detect whether said at least one haptic module is properly placed.

2. The augmented reality interactive rehabilitation system as claimed in claim 1, wherein said least one haptic module includes a plurality of haptic modules to be stacked one on the other.

3. The augmented reality interactive rehabilitation system as claimed in claim 2, wherein each of said haptic modules has a main body and at least one receiving space sensor, said main body having a receiving space that has an opening surrounded by said first end, said at least one receiving space sensor being disposed in said receiving space to detect whether said receiving space receives the other one of said haptic modules to form a stack.

4. The augmented reality interactive rehabilitation as claimed in claim 3, wherein each of said haptic modules further has a speaker disposed on said main body.

5. The augmented reality interactive rehabilitation system as claimed in claim 3, wherein said sensing modules are disposed on said first recess wall and said recess bottom surface.

6. The augmented reality interactive rehabilitation system as claimed in claim 1, wherein said haptic tool unit further includes a cue module disposed on said top surface of said holding seat for signalling that said at least one haptic module is properly placed into said holding seat.

7. The augmented reality interactive rehabilitation as claimed in claim 6, wherein said cue module has a light source.

8. The augmented reality interactive rehabilitation system as claimed in claim 6, wherein said cue module has a fragrance release device.

9. The augmented reality interactive rehabilitation system as claimed in claim 1, wherein said at least one haptic module is a cup, and said augmented reality image displays a simulation of a scene from a beverage shop.

10. The augmented reality interactive rehabilitation system as claimed in claim 9, wherein, when said identification module identifies a hand motion of picking up said cup, said augmented reality image displays that a beverage is prepared in a cup.

11. The augmented reality interactive rehabilitation system as claimed in claim 9, wherein, when said identification module identifies a hand motion of placing said cup into said holding seat, said augmented reality image displays that a cup containing a beverage is handed to a customer.

12. The augmented reality interactive rehabilitation system as claimed in claim 9, wherein, when identification module identifies a hand motion of placing said cup into said holding seat, said augmented reality eyewear device displays that a cup is washed and then placed in a ready use position.

* * * * *